(12) United States Patent
Gibson et al.

(10) Patent No.: US 7,797,029 B2
(45) Date of Patent: Sep. 14, 2010

(54) AUDITORY MIDBRAIN IMPLANT

(75) Inventors: Peter Gibson, South Coogee (AU); Thomas Lenarz, Hannover (DE); Minoo Lenarz, Hannover (DE); Miro Mackiewicz, Ryde (AU); John Parker, Roseville (AU); James Finlay Patrick, Roseville (AU)

(73) Assignee: Cochlear Limited, Lane Cove, New South Wales (AU)

( * ) Notice: Subject to any disclaimer, the term of this patent is extended or adjusted under 35 U.S.C. 154(b) by 604 days.

(21) Appl. No.: 10/493,675

(22) PCT Filed: Oct. 25, 2002

(86) PCT No.: PCT/AU02/01453

§ 371 (c)(1), (2), (4) Date: Aug. 26, 2004

(87) PCT Pub. No.: WO03/035168

PCT Pub. Date: May 1, 2003

(65) Prior Publication Data
US 2005/0004627 A1    Jan. 6, 2005

(30) Foreign Application Priority Data
Oct. 26, 2001 (AU) .................... PR8516

(51) Int. Cl.
A61B 5/04 (2006.01)
A61N 1/18 (2006.01)
A61N 1/05 (2006.01)

(52) U.S. Cl. .............. 600/378; 600/372; 600/393; 607/137; 607/148

(58) Field of Classification Search ........... 600/372–3, 600/377–9, 393; 607/115, 116, 137, 148
See application file for complete search history.

(56) References Cited

U.S. PATENT DOCUMENTS

| 4,819,647 | A | * | 4/1989 | Byers et al. .......... 607/116 |
| 5,496,369 | A | * | 3/1996 | Howard, III .......... 623/10 |
| 5,667,514 | A | * | 9/1997 | Heller .......... 606/108 |
| 5,697,975 | A |   | 12/1997 | Howard et al. |

(Continued)

FOREIGN PATENT DOCUMENTS

WO    WO95/21591    8/1995

(Continued)

OTHER PUBLICATIONS

International Search Report for PCT/AU02/01453 mailed Jan. 9, 2003.

(Continued)

*Primary Examiner*—Carl H Layno
*Assistant Examiner*—Natasha N Patel
(74) *Attorney, Agent, or Firm*—Connolly Bove Lodge & Hutz LLP

(57) ABSTRACT

An electrode array that is implantable within the inferior colliculus of the midbrain and/or other appropriate regions of the brain of an implantee and adapted to provide electrical stimulation thereto. The electrode array an elongate member having a plurality of electrodes mounted thereon in a longitudinal array. A delivery cannula for delivering the electrode array comprised of two half-pipes is also described.

32 Claims, 5 Drawing Sheets

U.S. PATENT DOCUMENTS

| | | | |
|---|---|---|---|
| 5,843,148 A * | 12/1998 | Gijsbers et al. | 607/116 |
| 5,902,236 A * | 5/1999 | Iversen | 623/23.65 |
| 6,129,685 A | 10/2000 | Howard | |
| 6,163,729 A * | 12/2000 | Kuzma | 607/137 |
| 6,309,410 B1 * | 10/2001 | Kuzma et al. | 607/137 |
| 6,374,143 B1 * | 4/2002 | Berrang et al. | 607/137 |
| 6,535,764 B2 * | 3/2003 | Imran et al. | 607/40 |
| 6,606,521 B2 * | 8/2003 | Paspa et al. | 607/116 |
| 7,033,326 B1 * | 4/2006 | Pianca et al. | 600/585 |
| 7,146,227 B2 * | 12/2006 | Dadd et al. | 607/137 |

FOREIGN PATENT DOCUMENTS

| | | |
|---|---|---|
| WO | WO01/60450 | 8/2001 |
| WO | 03/035168 | 5/2003 |

OTHER PUBLICATIONS

International Preliminary Examination Report for PCT/AU02/01453, dated Feb. 9, 2004.

Written Opinion for PCT/AU02/01453 mailed Apr. 24, 2003.

* cited by examiner

AUDITORY MIDBRAIN IMPLANT

CROSS REFERENCE TO RELATED APPLICATIONS

This application claims the priority of and is a national stage application of PCT Application No. PCT/AU02/01453, entitled, "Auditory Midbrain Implant," filed on Oct. 25, 2002, which claims the priority of Australian Provisional Application No. PR 8516, filed on Oct. 26, 2001. The entire contents and disclosures of the above applications are hereby incorporated by reference.

FIELD OF THE INVENTION

The present invention relates to an implant system that can be positioned in the inferior colliculus of the midbrain of an implantee to provide a hearing sensation to persons with hearing loss.

BACKGROUND OF THE INVENTION

Hearing loss can be due to many different causes. One type of hearing loss is conductive hearing loss which occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

Cochlear implant systems have been developed for persons with sensorineural hearing loss which bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

While cochlear implants have proven very successful in restoring hearing sensation to many people, persons with bilateral neural deafness are unable to benefit from such technology due to the missing transmission of electrical signals to the second neuron of the auditory pathway. Such persons are mainly patients suffering from neurofibromatosis type II and bilateral acoustic neuromas and, less frequently, patients with congenital missing auditory nerve or traumatic lesions of the auditory nerve.

Restoration of hearing to such persons is to date only possible with electrical stimulation central to the lesion site, eg. the cochlear nucleus. For example, a surface electrode plate can be placed on the surface of the cochlear nucleus in the lateral recess. While several hundred patients have now received such implants and had some restoration of hearing, the results in terms of performance are below that now achieved by cochlear implants. Postulated explanations for the results include the distortion of the anatomy at the cochlear nucleus due to the tumour size or previous treatment including gamma knife therapy, unfavourable exposure with limited visibility of the stimulation site, and the unfavourable tonotopic organisation of the nucleus with irregular frequency layer organisation in relation to the plane of the electrode plate.

With the above background in mind, there is a need to provide an implant system that provides a hearing sensation to persons unable to derive any benefit from conventional hearing aids and cochlear implant systems.

Further to this, with the benefits of electrical stimulation applied to specific parts of the brain to treat disorders such as Parkinson's Disease, Dyskinesia etc now being realised, there is a need to provide an implant system that can be easily adapted to apply such treatment.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implant system that provides a hearing sensation to an implantee, the system comprising an electrically stimulating electrode implantable within the inferior colliculus of the midbrain of the implantee to provide electrical stimulation thereto.

An advantage of placing the electrode within the inferior colliculus is that the anatomy of this site is generally not distorted by the presence of tumours, such as neurofibromatosis type II, or previous treatment thereof. The inferior colliculus can also typically be exposed with relatively good visibility and is relatively easy to identify.

The inferior colliculus is composed of several subdivisions; the central nucleus (ICC), the dorso-medial nucleus (DM), the dorsal cortex (DC) and the lateral nucleus (LN). Virtually every kind of pre-processed auditory information from the brainstem is collected in the ICC, which from the point of tonotopicity, has a highly organised pattern, with layers mostly parallel to the surface of the inferior colliculus. The whole frequency range of hearing is represented by the isofrequency planes in the inferior colliculus, which are ordered by low frequencies represented dorsolaterally and high frequencies ventromedially.

In a further aspect, the present invention is an electrode array that is insertable in the brain of an implantee, the electrode array having a plurality of electrodes mounted thereon.

In one embodiment, the electrodes are mounted on an elongate member. In one embodiment of both aspects, the elongate member can have between about 4 and 80 electrodes, and more preferably about 20 electrodes, mounted thereon.

The electrodes can be disposed in a longitudinal array on the elongate member. The electrodes can be equally spaced along the elongate member. The electrodes can be adapted to apply a preselected tissue stimulation to the inferior colliculus, and/or other appropriate regions of the brain, such as the Subthalamic Nucleus (STN), the Globus Pallidus (GPi), and the Thalamus. The electrodes are preferably adapted to provide multi-channel stimulation of these regions of the brain.

Each electrode can consist of a single or several penetrating pins. In another embodiment, each electrode can comprise a ring. In another embodiment, the electrodes may comprise half rings, flat pads or multiple pads around the circumference of the elongate body. In one embodiment, each of the electrodes can be identical in form. In another embodiment, at least one of the electrodes can have a different form from at least one of the other electrodes. The pins can be made of a suitable electrically conducting material, such as platinum or platinum-iridium alloy. The electrodes preferably have a surface area sufficiently large so as to not exceed charge density limits.

The spacing of the electrodes is preferably such that different frequency layers of the inferior colliculus can be stimulated. Each electrode can have a width of between about 50 and about 2000 microns, more preferably about 100 microns. The spacing between the electrodes can be between about 50 and about 2000 microns, more preferably about 100 microns. The pitch of the electrodes can be between about 50 microns and about 2000 microns, more preferably about 200 microns. In one embodiment, the array has a length of between about 2 mm and about 6 mm, more preferably about 4 mm long.

In a preferred embodiment, the elongate member has a tip at a distal end that assists in passage of the member into the brain or portions thereof, such as the inferior colliculus, while causing relatively minimal trauma to the sensitive tissues of the brain. The diameter of the elongate member can begin to decrease proximate the distal end to the tip. The tip can be formed of a biocompatible material, such as stainless steel, platinum-iridium alloy or other metals, and can be machinable to a desired geometry.

The tip can be formed from a material selected from the group comprising silicone, polytetrafluoroethylene (PTFE), polyurethane, other polymers, and polymer-coated substrates such as silicone-coated platinum and parylene-coated platinum. The tip can have a relatively small radius, however, a relatively larger radius tip could be used, eg. a hemisphere with the radius matching the diameter of the body of the electrode.

The elongate member can have a body formed from a suitable biocompatible material. In one embodiment, the body can be formed from a material selected from the group comprising silicone, polyimide, polyurethane, PTFE, and other polymers.

The body is preferably relatively stiff to allow the elongate member to penetrate the surface of the inferior colliculus and be inserted at a desired depth therein. The elongate body can have a diameter in the range of about 0.2 mm to about 2 mm, more preferably about 0.5 mm.

In one embodiment, the elongate member can have a stiffening element extending at least partially therethrough. The stiffening element can be non-removably positioned in the elongate member. In another embodiment, the stiffening element can comprise a removable stylet. The stiffening element can comprise a wire. The wire can be circular or non-circular in cross-section. The stylet can be formed of a suitable metallic material, such as stainless steel. In another embodiment, the stiffening element can be formed from a bioresorbable material. The stiffening element can extend through a lumen formed in the elongate member and the lead. The lumen preferably extends axially through the elongate member and the lead.

In one embodiment, a stiffening stylet can be used to maintain the elongate member in a configuration suitable for insertion into the desired region. Once positioned, the stylet would preferably be removed from the member and the lead simply by withdrawing the stylet from the lumen. In this regard, the lead needs to be of a suitable thickness to enclose the stylet and the conducting wires connecting the electrodes to the stimulator/receiver unit.

In an alternative embodiment, the stiffening element can have a stepped outer surface. In such an arrangement, the element can have a section of relatively narrower dimensions that is inserted into the elongate member and a section of relatively wider dimensions that is normally positioned external of the array. In this arrangement, each section can be made from the same material or from a different material such as stainless steel, titanium, iridium etc. This will allow the relative rigidity of each section to the stiffening element to be altered to suit the specific purpose. As can be appreciated, this arrangement does not require a lumen extending from the array through the lead as only a short lumen is required through the array.

To remove the stylet following correct insertion of the array, an additional holding tool can be employed to maintain the array in position. Such a tool can be placed behind the skirt of the array whilst the stylet is being removed. This has the benefit in that the size of the lead can be significantly reduced, as it no longer has to accommodate a stiffening stylet. A relatively thinner lead also has the advantage of being relatively more flexible. This is important when one considers that the brain is in constant pulsing motion and therefore a lead positioned within the brain could cause complications if it is of a size and rigidity that would cause pressure on the structures of the brain. As it is expected that the cerebellum will need to be depressed to allow insertion of the electrode, the lead therefore passes over the top of the cerebellum following electrode insertion. Once the cerebellum is released it will resume its shape to fill up the skull cavity and as such the lead needs to be relatively flexible to so move with the cerebellum and not cut or bruise the cerebellum. Therefore, reducing the size of the lead and increasing its flexibility is important in the present application. Further to this, by requiring only a short lumen extending into the array, the potential for creating a passage for infection to travel from the stimulator/receiver unit to the array is reduced, reducing the risk of such infections and meningitis.

In yet another aspect, the present invention is a stiffening element for a brain stimulating electrode array wherein the stiffening element has a stepped outer surface with the element having a section of relatively narrower dimensions that is inserted into the elongate member and a section of relatively wider dimensions that is normally positioned external of the array.

In this aspect, the stiffening element can have the features as are defined herein.

As mentioned, in one embodiment of any one of the aspects, the elongate member can have a cuff or skirt positioned about the body at a predetermined distance from the distal tip. The skirt or cuff can be adapted to collapse on insertion of the elongate member through a delivery cannula but expand on exiting a distal end of the cannula. The skirt or cuff can be formed from Dacron™.

The skirt or cuff is preferably spaced a distance of between about 6 and 6.5 mm from the distal tip and is adapted to stabilise the elongate member in the inferior colliculus and ensure the elongate member does not migrate further into the inferior colliculus following correct placement.

The skirt can have a plurality of fold lines and/or ribs formed therein so as to allow the skirt to collapse on insertion through the delivery cannula. In one embodiment, the skirt can be adapted to collapse and/or expand in a spiral fashion.

Each electrode is preferably individually connected to at least one wire which is electrically insulated from other wires extending to other electrodes in the array. The wires preferably extend through the elongate member to at least, and preferably beyond, the proximal end of the elongate member. The wires can extend through a lead that extends outwardly from the proximal end of the elongate member.

Each elongate member can have a stiffening element extending at least partially therethrough. The stiffening element can be non-removably positioned in the elongate member. In another embodiment, the stiffening element can comprise a removable stylet. The stiffening element can comprise a wire. The wire can be circular or non-circular in cross-section. The stylet can be formed of a suitable metallic material, such as stainless steel. In another embodiment, the stiffening element can be formed from a bioresorbable material. The stiffening element can extend through a lumen formed in the elongate member. Such a lumen preferably extends axially through the elongate member.

In a further embodiment, one or more bioactive agents can be delivered through the lumen of the elongate member. In one embodiment, the bioresorbable stiffening element can have one or more bioactive agents incorporated therein. One or more ports can be formed in the elongate member to allow the bioactive agents to elute into the site of implantation of the elongate member. The one or more ports can be at or adjacent the tip of the elongate member or distal thereto. The ports can also be adapted to allow body fluids, such as cerebrospinal fluid, to enter the lumen. The entry of the body fluids can be used to cause or continue resorption of a bioresorbable stiffening element positioned therein.

In one embodiment, the implant system further comprises a stimulator that outputs stimulation signals to the electrodes of the electrode array according to the first aspect. Such a stimulator can also be used in conjunction with the electrode array of the further aspect. For the purpose of this description, the features as hereunder defined can be used in association with the invention as defined in either aspect.

The stimulator is preferably electrically connected to the elongate member by way of an electrical lead, including the lead defined above. The lead can include the one or more wires extending from each electrode of the array mounted on the elongate member. In one embodiment, the lead can extend from the elongate member to the stimulator or at least the housing thereof.

In one embodiment, the lead is continuous with no electrical connectors, at least external the housing of the stimulator, required to connect the wires extending from the electrodes to the stimulator. One advantage of this arrangement is that there is no requirement for the surgeon implanting the device to make the necessary electrical connection between the wires extending from the electrodes and the stimulator.

The stimulator is preferably positioned within a housing that is implantable within the head of the implantee. The housing for the stimulator is preferably implantable within a bony well in the bone behind the ear posterior to the mastoid.

When implantable, the housing preferably contains, in addition to the stimulator, a receiver. The receiver is preferably adapted to receive signals from a controller. The controller is, in use, preferably mounted external to the body of the implantee such that the signals are transmitted transcutaneously between the controller and the receiver.

Signals can preferably travel from the controller to the receiver and vice versa. The receiver can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms developed for cochlear implant systems. The encoded sequence is transferred to the implanted stimulator/receiver device using the transmitter and receiver coils. The implanted stimulator/receiver device demodulates the FM signals and allocates the electrical pulses to the appropriate attached electrode by an algorithm which is consistent with the chosen speech coding strategy.

The external controller preferably further comprises a power supply. The power supply can comprise one or more rechargeable batteries. The transmitter and receiver coils are used to provide power via transcutaneous induction to the implanted stimulator/receiver device and the electrode array.

While the implant system can rely on external componentry, in another embodiment, the controller, including the microphone, speech processor and power supply can also be implantable. In this embodiment, the controller can be contained within a hermetically sealed housing or the housing used for the stimulator.

According to a still further aspect, the present invention is a delivery cannula for delivering an elongate member having an array of electrodes mounted thereon to a desired location in the brain of an implantee.

In one embodiment, the elongate member and/or the electrode array of this aspect can have the features of these devices as defined herein.

The cannula can be used in stereotactic placement of the elongate member in the brain, such as in the inferior colliculus, the Subthalamic Nucleus (STN), the Globus Pallidus (GPi), and/or the Thalamus of the brain of the implantee.

The cannula can be comprised of two or more longitudinal portions. In one embodiment, the cannula can be comprised of two half-pipes joined at respective longitudinal joins. The cannula when assembled can be cylindrical in form. Other forms can, however, be envisaged.

The two half-pipes are preferably held together by a holding device adapted to be positioned outside the skull during use of the cannula. The holding device can be a mechanical holding device, such as a ring, that removably surrounds the half-pipes. The holding device can also comprise a polymer sheath, such as a parylene coating, that is removable from the cannula. The parylene coating can be in the form of a thin film having a thickness of about 3-5 microns. A wire that slits the sheath along the joins of the half-pipes can cut the sheath. In another embodiment, the sheath can be cut off the cannula using a scalpel or hot knife. Still further, the holding device can comprise respective pins that extend the length of the cannula and join the respective edges of the half-pipes together.

The disassembly of the delivery cannula from around the elongate member and/or the lead extending therefrom is advantageous when the lead is non-removably connected from the elongate member back to the stimulator and/or the housing therefor. The cannula can be removed from at least around the lead by being disassembled following insertion of the elongate member into the brain.

In a still further aspect, the present invention is a method of providing electrical stimulation to the brain of an implantee, the method comprising the steps of:

(i) implanting at least one electrode array within a portion of the brain of the implantee; and (ii) delivering electrical stimulation through the array to said portion of the brain.

In a preferred embodiment, step (i) comprises the step of implanting an elongate member having an array of electrodes as is defined herein.

In one embodiment, the method can be used to provide a hearing sensation to an implantee. In this embodiment, step (i) comprises implanting the electrode array in the inferior colliculus of the brain of the implantee and step (ii) comprises delivering electrical stimulation through the array to the inferior colliculus.

In yet another embodiment, step (i) can comprise a step of implanting the electrode array in the Subthalamic Nucleus (STN), the Globus Pallidus (GPi), and/or the Thalamus of the brain of the implantee, with step (ii) comprising delivering electrical stimulation to these portions of the brain.

In a further embodiment, step (i) of the method preferably comprises the steps of:

(a) identifying the position of the portion of the brain of the implantee that is to receive the electrode array;

(b) mounting a stereotactic frame to the implantee's head; and (c) inserting the electrode array into said portion of the brain using the stereotaxis.

In this embodiment, step (a) can comprise a step of identifying the inferior colliculus of the midbrain. The position of the inferior colliculus can preferably be localised using magnetic resonance imaging (MRI) with exact intraoperative placement adjusted by direct electrical stimulation of the inferior colliculus and recording of electrically evoked auditory potentials. In this approach, the electrode can be placed under local anaesthesia while verifying the optimum placement by psychophysical measures and according to the patient's recommendations. The method therefore includes a step of confirming the correct position of the electrodes of the array. This can be confirmed during surgery on a conscious patient by matching each electrode position with the frequency of best response for acoustic stimuli applied to the contralateral ear. This step will confirm that the electrodes cover the chosen acoustic frequency range. For patients with no acoustic hearing in the contralateral ear, confirmation of frequencies will be based on patient judgement in response to stimulation of the different electrodes. To add electrodes, the array can be advanced into the inferior colliculus. Addition to the range of frequencies represented will be confirmed as the electrode array is advanced.

The stereotactic implantation can be performed through a burr hole, with the stimulator/receiver device placed subperiostally in a bony bed behind the pinna.

Once in position, the elongate member can be fixed at the skull and the stereotactic frame removed.

There are two other presently envisaged methods for placement of the electrode array in the inferior nucleus.

The first envisaged method involves placement during removal of an acoustic neuroma. In this case, the inferior colliculus can be reached by a medially extended, lateral suboccipital approach, with downward retraction of the cerebellum. The electrode can be inserted from laterally to antero-medially. This direction of penetration is substantially perpendicular to the organisation of the frequency layers in the central nucleus of the inferior nucleus. The placement will be performed at the same surgical setting, after removal of the acoustic neuroma. After implantation, the electrode lead is preferably passed through an opening in the dura and can extend toward and preferably to the stimulator/receiver device, such as the device defined herein.

The second envisaged method involves using a medial sub-occipital (infratentorial-supracerebellar) approach. Using this approach, removal of an acoustic neuroma in an implantee with neurofibromatosis type II who has already lost his/her hearing and has multiple other tumours in the CNS is not absolutely necessary, unless the tumour is very large and has endangered other cranial nerves (such as the facial nerve) or is compressing the brainstem. In this approach, after downward retraction of the cerebellum, direct exposure of the inferno colliculus is possible and the electrode can be placed under direct vision into the inferior colliculus.

In yet another aspect the present system is an electrode array for the treatment of movement disorders and other neurological disorders, such as Parkinson's disease, Dyskinesia, Tourette's Syndrome, Essential Tremor and Epilepsy, to name a few.

In this regard, the electrode array preferably has a plurality of electrodes capable of being inserted into appropriate regions of the brain, such as the Subthalamic Nucleus (STN), the Globus Pallidus (GPi), and the Thalamus for multi-channel stimulation of these regions. By providing an increased number of electrodes inserted into these regions with the present invention, treatment can be optimised to suit the specific disorder being addressed.

BRIEF DESCRIPTION OF THE DRAWINGS

By way of example only, preferred embodiments of the invention are now described with reference to the accompanying drawings, in which.

PREFERRED MODE OF CARRYING OUT THE INVENTION

Figure 1:
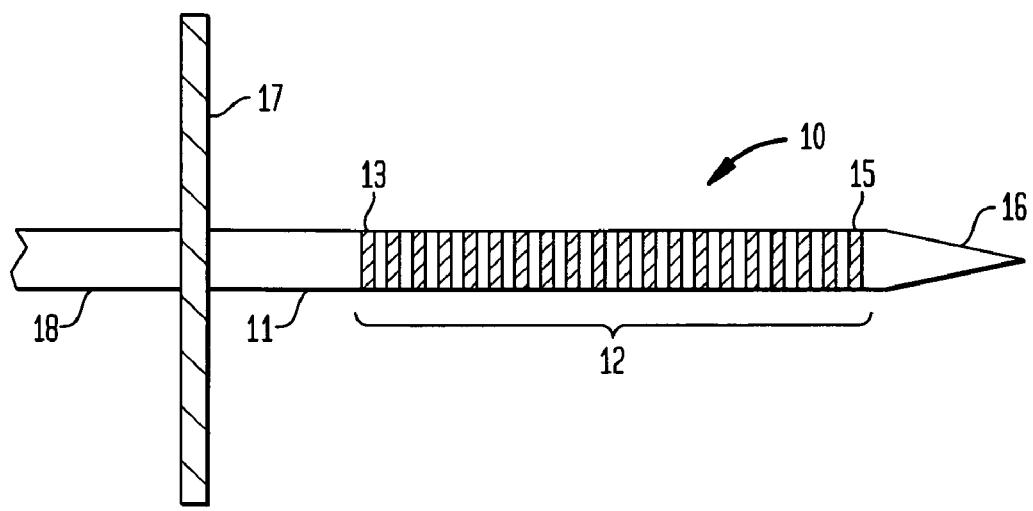
FIG. 1 is a side elevation view of one embodiment of an electrode array according to the present invention.
Figure 2:
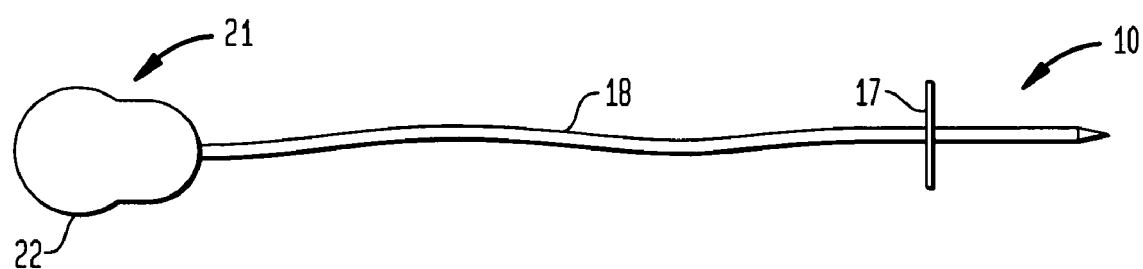
FIG. 2 is a plan view of the electrode of FIG. 1 but also depicting the lead extending back to the stimulator/receiver of the implant system.

One embodiment of an electrode array that is implantable within the inferior colliculus of the midbrain of an implantee and adapted to provide electrical stimulation thereto is depicted generally as 10 in FIGS. 1 and 2.

While described as implantable in the inferior colliculus, it is to be appreciated that the electrode array and the system in general as described below can, with necessary appropriate modification, also be used in the treatment of movement disorders and other neurological disorders, such as Parkinson's disease, Dyskinesia, Tourette's Syndrome, Essential Tremor and Epilepsy, to name a few. In this regard, it is to be understood that the electrode array is also suitable for insertion into other appropriate regions of the brain, such as the Subthalamic Nucleus (STN), the Globus Pallidus (GPi), and the Thalamus to provide multi-channel stimulation of these regions. By providing an increased number of electrodes inserted into these regions with the present invention, treatment can be optimised to suit the specific disorder being addressed.

As determined by the present inventors, an advantage of placing the electrode array within the inferior colliculus is that the anatomy of this site is generally not distorted by the presence of tumours, such as a neurofibromatosis type II tumour, or previous treatment thereof. The inferior colliculus can also be exposed with relatively good visibility and is relatively easy to identify.

Implantation within the inferior colliculus is envisaged as desirable as virtually every kind of pre-processed auditory information from the brainstem is collected in the inferior colliculus, which from the point of tonotopicity, has a highly organised pattern, with layers mostly parallel to the surface of the inferior colliculus. The whole frequency range of hearing is represented by the isofrequency planes in the inferior colliculus, which are ordered by low frequencies represented dorsolaterally and high frequencies ventromedially.

In the depicted embodiment, the electrode array has an elongate member 11 having a plurality of electrodes 12 mounted thereon. In this embodiment, the elongate member has twenty electrodes 12 disposed in a longitudinal array on the elongate member 11. As depicted, the electrodes 12 can be equally spaced along the elongate member 11 and adapted to apply a preselected tissue stimulation to the inferior colliculus.

In this embodiment, each electrode 12 comprises a platinum or platinum-iridium alloy ring. In another embodiment, the electrodes may comprise half rings, flat pads, or multiple pins or pads around the circumference of the elongate body 11.

The spacing of the electrodes is preferably such that different frequency layers of the inferior colliculus can be stimulated. In the depicted embodiment, each electrode has a width of 100 microns, with the spacing between the electrodes being 100 microns. The total length of the depicted elongate member 11 from the outer (as depicted, the left) edge of ring one 13 to the outer (as depicted, the right) edge of ring twenty 15 is 4.1 mm.

The depicted elongate member 11 has a tip 16 at a distal end that assists in passage of the member 11 into the brain or portions thereof, such as the inferior colliculus, while causing relatively minimal trauma to the sensitive tissues of the brain. As depicted, the diameter of the elongate member can begin to decrease proximate the distal end to the tip. The commencement of the tapering of the tip 16 is spaced 0.2 mm from the outer edge of ring twenty 15 and extends for a length of 1 mm.

The tip can be formed of a biocompatible material, such as stainless steel, platinum-iridium alloy or other metals and be machinable to a desired geometry. The tip can be formed from a material selected from the group comprising silicone, polytetrafluoroethylene (PTFE), polyurethane, other polymers, and polymer-coated substrates such as silicone-coated platinum and parylene-coated platinum.

The elongate member 11 can have a body formed from a suitable biocompatible material. In one embodiment, the member 11 can be formed from a material selected from the group comprising silicone, polyimide, polyurethane, PTFE, and other polymers.

The member 11 is preferably sufficiently relatively stiff to allow the elongate member 11 to penetrate the surface of the inferior colliculus and be inserted at a desired depth therein. The depicted elongate member has a diameter of 0.5 mm in the region apart from the tip 16.

The member 11 can have a stiffening element extending at least partially therethrough. The stiffening element can be non-removably positioned in the elongate member 11. In another embodiment, the stiffening element can comprise a removable stylet. The stiffening element can comprise a wire. The wire can be circular or non-circular in cross-section. The stylet can be formed of a suitable metallic material, such as stainless steel. In another embodiment, the stiffening element can be formed from a bioresorbable material. The stiffening element can extend through a lumen formed in the elongate member and the lead 18. The lumen preferably extends axially through the elongate member 11 and lead 18.

In the embodiment shown in FIG. 2, a stiffening stylet can be used to maintain the elongate member in a configuration suitable for insertion into the desired region. Once positioned, the stylet is removed from the member 11 and the lead 18 simply by withdrawing the stylet from the lumen. In this regard, the lead 18 is of a suitable thickness to enclose the stylet and the conducting wires connecting the electrodes to the stimulator/receiver unit 21.

Figure 5:
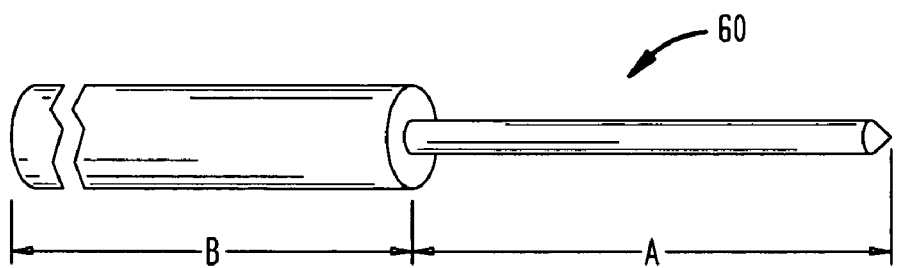
FIG. 5 is a perspective view of a stylet for use in the array according to the present invention.
Figure 6:
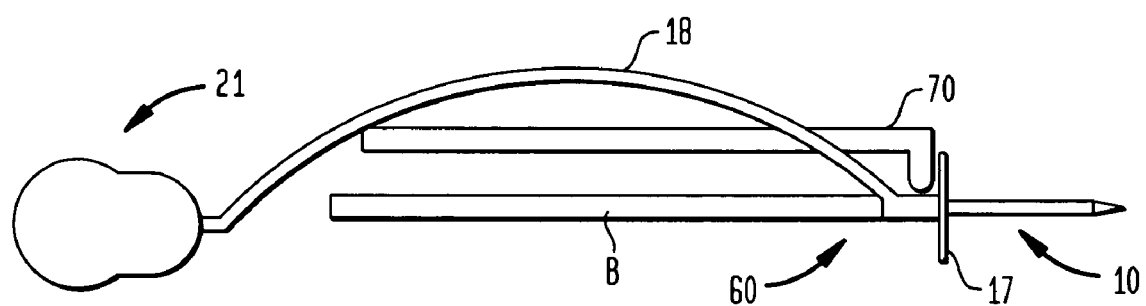
FIG. 6 is a simplified view of another arrangement for mounting a stylet in an array according to the present invention.

In an alternative embodiment, the stiffening element can be a stepped stylet 60 as shown in FIG. 5. In such an arrangement, the narrower section shown as A is inserted into the elongate member 11 for insertion, with the wider section B being external of the array 10 as is shown in FIG. 6. Each of the sections A and B can be made from the same material, for example stainless steel, titanium, iridium or tungsten, or each section could be made from a different material. This may allow for one section, eg section A, being more/less rigid than the other section, eg section B. As can be appreciated, this arrangement does not require a lumen extending from the array 10 through the lead 18 as only a short lumen is required through the array 10.

To remove the stylet 60 following correct insertion of the array 10, an additional holding tool 70 can be employed to maintain the array 10 in position. Such a tool can be placed behind the skirt 17 of the array 10 whilst the stylet 60 is being removed. This arrangement has the benefit in that the size of the lead 18 can be significantly reduced and thus the rigidity, as it no longer has to accommodate a stiffening stylet. This is important when one considers that the brain is in constant pulsing motion and therefore a lead positioned within the brain could cause complications if it is of a size and rigidity that would cause pressure on the structures of the brain. Therefore, reducing the size of the lead and increasing its flexibility is important in the present application. Further to this, by requiring only a short lumen extending into the array 10, the potential for creating a passage for infection to travel from the stimulator/receiver unit to the array 10 is reduced, reducing the risk of such infections and meningitis. Also, having a short stylet in the shorter lumen will reduce the friction when the stylet is withdrawn. This therefore allows for a gentler surgical procedure then that which would require removal of a stylet from a longer lumen.

Figure 7:
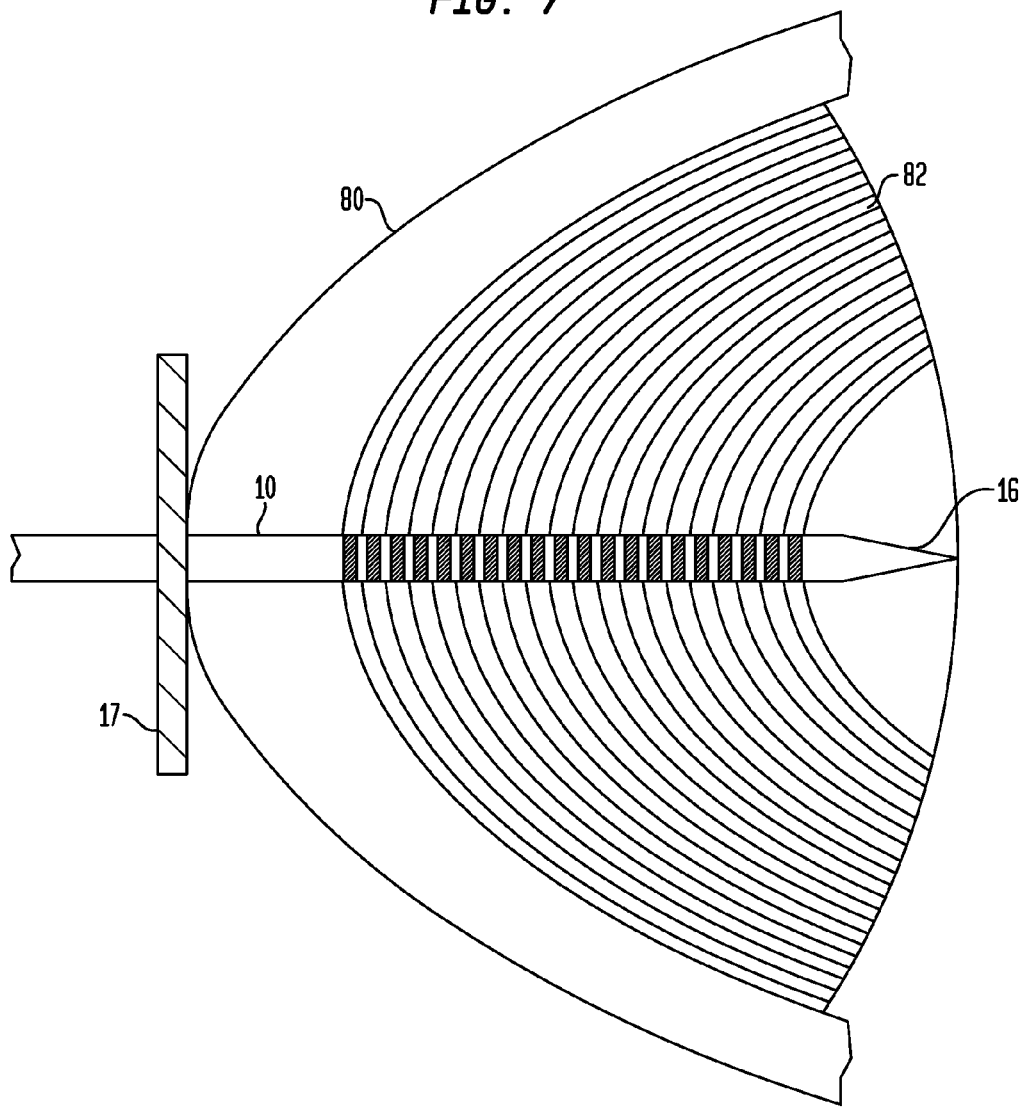
FIG. 7 is a simplified view of the Inferior colliculus (IC) and the central nucleus (ICC) of the brain of an implantee having received the array according to the present invention.

As depicted, the elongate member 11 can have a skirt 17 positioned about the member at a predetermined distance from the tip 16. The skirt in the depicted embodiment has a radius of 4 mm and is 0.2 mm thick. The skirt 17 can be adapted to collapse on insertion of the elongate member 11 through a delivery cannula 30, as described below, but expand on exiting a distal end of the cannula 30. The skirt can be formed from Dacron™. The depicted skirt 17 is spaced a distance of 1.2 mm from the outer edge of ring one 13 and is adapted to stabilise the elongate member 11 in the inferior colliculus and ensure the elongate member 11 does not migrate further into the inferior colliculus following correct placement. As shown in FIG. 7, the spacing from the outer edge of ring one 13 to the skirt caters for the distance between the Inferior colliculus (IC) and the central nucleus (ICC) where every kind of preprocessed auditory information from the brainstem is collected in a highly organised and known pattern as shown, which can be stimulated by the electrodes.

The skirt 17 can have a plurality of fold lines and/or ribs formed therein so as to allow the skirt to collapse on insertion through the delivery cannula. In one embodiment, the skirt 17 can be adapted to collapse and/or expand in a spiral fashion.

Each electrode 12 is individually connected to at least one wire which is electrically insulated from other wires extending to other electrodes 12 in the array. The wires (not visible) extend through the elongate member 11 and out the proximal end of the elongate member 11 through lead 18.

The lead 18 can extend to a stimulator/receiver 21 that outputs stimulation signals to the electrodes 12 of the elongate member 11. The depicted lead 18 from the stimulator/receiver 21 to the skirt 17 has a length of 180 mm and a diameter of 1.1 mm or less.

In the depicted embodiment, the lead 18 is continuous with no electrical connectors, at least external the housing of the stimulator/receiver 21, required to connect the wires extending from the electrodes 12 to the stimulator/receiver 21. One advantage of this arrangement is that there is no requirement for the surgeon implanting the device to make the necessary electrical connection between the wires extending from the electrodes 12 and the stimulator/receiver 21 during the surgery.

In an alternative embodiment, the lead 18 could be removably connectable to the stimulator/receiver 21 through a connector system. Such a connector system provides a surgeon the ability to explant the stimulator/receiver 21 without needing to remove and reimplant the electrode array 10.

The stimulator/receiver 21 is positioned within a hermetically sealed housing 22 that is implantable within a bony well in the bone behind the ear posterior to the mastoid of the implantee.

The stimulator/receiver is also adapted to receive signals from a controller. The controller is, in use, preferably mounted external to the body of the implantee such that the signals are transmitted transcutaneously through the implantee.

Signals can preferably travel from the controller to the stimulator/receiver 21 and vice versa. The stimulator/receiver can include a receiver coil adapted to receive radio frequency (RF) signals from a corresponding transmitter coil worn externally of the body. The radio frequency signals can comprise frequency modulated (FM) signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms developed for cochlear implant systems. The encoded sequence is transferred to the implanted stimulator/receiver 21 using the transmitter and receiver coils. The implanted stimulator/receiver 21 demodulates the FM signals and allocates the electrical pulses to the appropriate attached electrode 12 by an algorithm which is consistent with the chosen speech coding strategy.

The external controller can further comprise a power supply. The power supply can comprise one or more rechargeable batteries. The transmitter and receiver coils are used to provide power via transcutaneous induction to the implanted stimulator/receiver 21 and the electrode array 10.

While the implant system can rely on external componentry, in another embodiment, the controller, including the microphone, speech processor and power supply can also be implantable. In this embodiment, the controller can be contained within a hermetically sealed housing or the housing 22 used for the stimulator/receiver 21.

Where present, one or more bioactive agents can be delivered through a lumen of the elongate member 11, including a lumen adapted to receive a stiffening element. In one embodiment, a bioresorbable stiffening element having one or more bioactive agents incorporated therein can be positioned in the lumen. One or more ports can be formed in the elongate member 11 to allow the bioactive agents to elute into the site of implantation of the elongate member 11. The one or more ports can be at or adjacent the tip 16 of the elongate member 11 or distal thereto. The ports can also be adapted to allow body fluids, such as cerebrospinal fluid, to enter the lumen. The entry of the body fluids can be used to cause or continue resorption of a bioresorbable stiffening element positioned therein.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

Figure 3A:
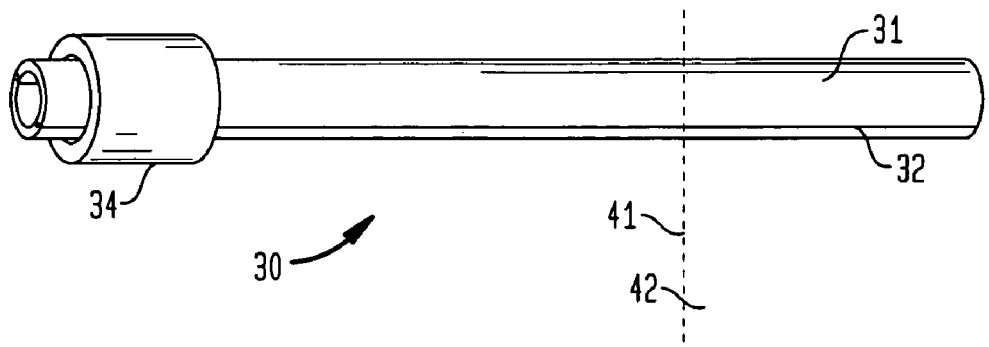
FIG. 3a is a perspective view and FIG. 3b an end elevation view of one embodiment of a delivery cannula for use in the positioning of an electrode, such as that depicted in FIG. 1.
Figure 3B:
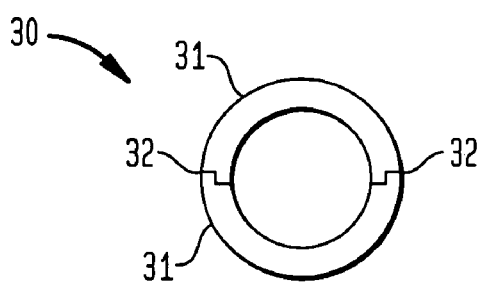

One embodiment of a delivery cannula for delivering an elongate member 11 having an array of electrodes 12 mounted thereon to a desired location in the brain of an implantee is depicted generally as 30 in FIGS. 3*a* and 3*b*.

The cannula 30 can be used in stereotactic placement of the elongate member 11 in the brain, such as in the inferior colliculus of the midbrain of the implantee. As depicted in FIG. 3*a* the cannula 30 extends through the surface 41 of the skull 42 and is used to ensure accurate delivery of the elongate member 11 into the inferior colliculus.

The depicted cannula 30 is comprised of two longitudinal half-pipe portions 31, joined at respective longitudinal joins 32. The cannula 30, when assembled, is cylindrical in form. Other forms can, however, be envisaged.

The two half-pipes 31 are depicted held together in FIG. 3*a* by a ring 34 that removably surrounds the half-pipes 31. On removal of the ring 34, the half pipes 33 can disengage along the joins 32 and be removed from around the lead 18.

Figure 4:
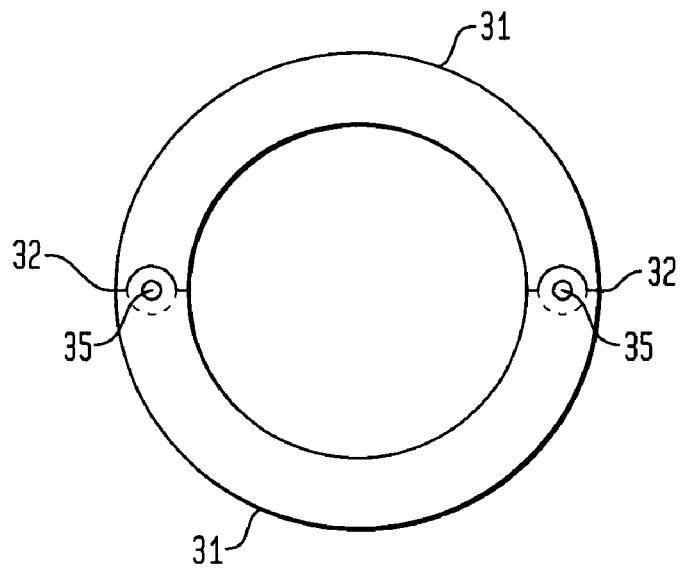
FIG. 4 is an end elevation view of an alternative embodiment of a delivery cannula for use in the positioning of an electrode.

In another embodiment, the half-pipes 31 can be held together by a polymer sheath, such as a parylene coating, that is removable from the cannula 30. The parylene coating can be in the form of a thin film having a thickness of about 3-5 microns. A wire that slits the sheath along the joins 32 of the half-pipes 31 can cut the sheath. In another embodiment, the sheath can be cut off the cannula using a scalpel or hot knife. Still further, the half-pipes 31 can be held together by respective pins 35 that extend the length of the cannula 30 and join the respective edges of the half-pipes 31 together, as is depicted in FIG. 4.

The disassembly of the delivery cannula 30 from around the elongate member 11 and/or the lead 18 extending therefrom is advantageous when the lead 18 is non-removably connected from the elongate member 11 back to the stimulator/receiver housing 22. The cannula 30 can be removed from at least around the lead 18 by the surgeon by being disassembled following insertion of the elongate member 11 into the brain.

In use, the elongate member 11 is implanted within the inferior colliculus of the implantee. Electrical stimulation is then delivered to the inferior colliculus by the electrodes 12.

The step of implanting the elongate member 11 can comprise the steps of:

(a) identifying the position of the inferior colliculus in the implantee;

(b) mounting a stereotactic frame to the implantee's head; and (c) inserting the elongate member 11 into the inferior colliculus of the midbrain using the stereotaxis.

The position of the inferior colliculus can be localised using magnetic resonance imaging (MRI) with exact intraoperative placement adjusted by direct electrical stimulation of the inferior colliculus and recording of electrically evoked auditory potentials. In this approach, the elongate member 11 can be placed under local anaesthesia while verifying the optimum placement by psychophysical measures and according to the patient's recommendations. The method therefore includes a step of confirming the correct position of the member 11. This can be confirmed during surgery on a conscious patient by matching the position of each electrode 12 with the frequency of best response for acoustic stimuli applied to the contralateral ear. This step will confirm that the electrodes 12 cover the chosen acoustic frequency range. For patients with no acoustic hearing in the contralateral ear, confirmation of frequencies will be based on patient judgement in response to stimulation of the different electrodes 12. To add electrodes 12, the elongate member 11 can be advanced into the inferior colliculus. Addition to the range of frequencies represented will be confirmed as the elongate member 11 is advanced.

The stereotactic implantation can be performed through a burr hole, with the stimulator/receiver 21 placed subperiostally in a bony bed behind the pinna.

Once in position, the elongate member 11 can be fixed at the skull 42 and the stereotactic frame removed.

Figure 8:
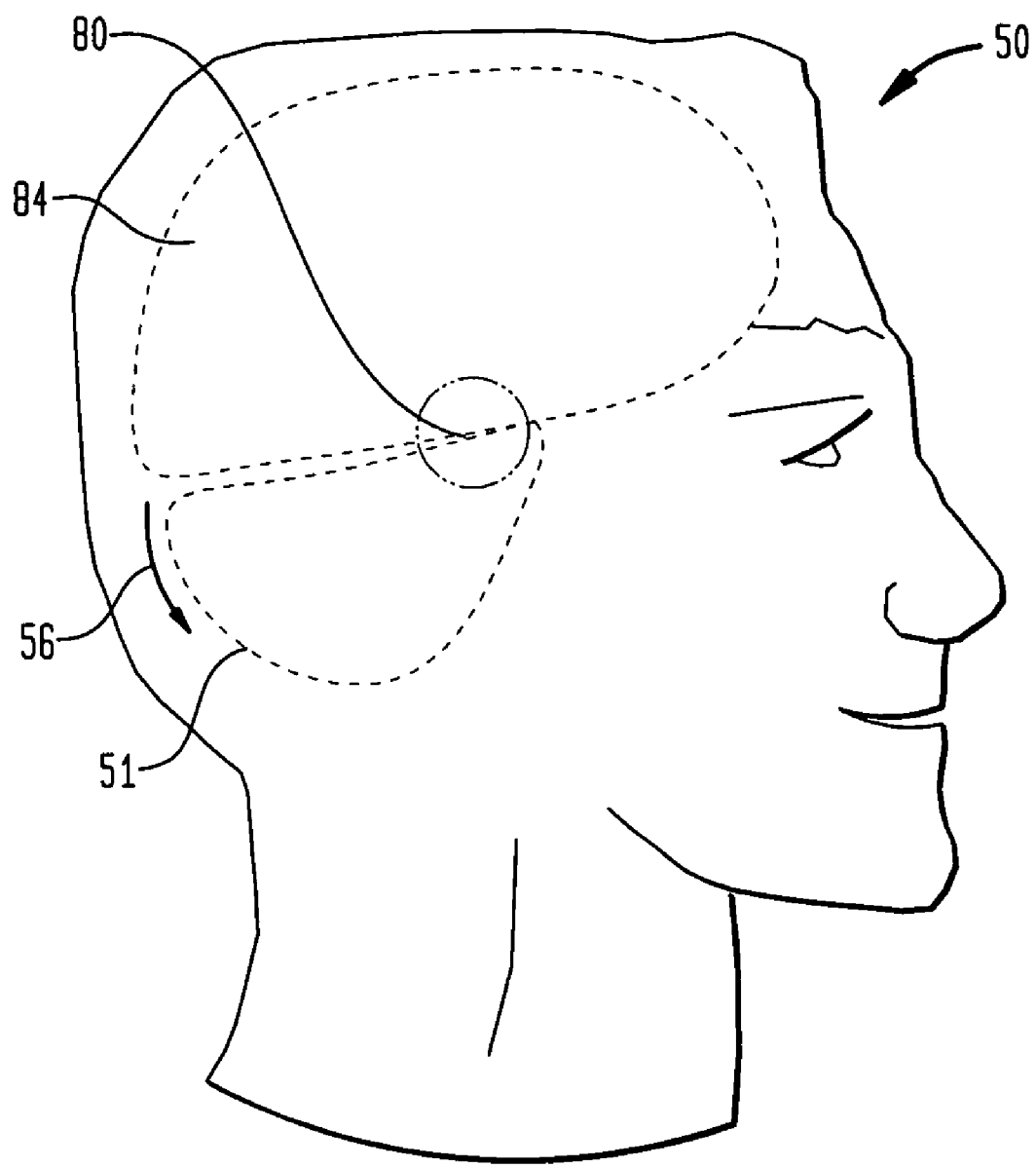
FIG. 8 is a simplified view of the brain and cerebellum of an implantee.

There are two other envisaged methods for placement of the electrode array on the elongate member 11. The first involves placement during removal of an acoustic neuroma. The inferior colliculus 80 can be reached by a medially extended, lateral suboccipital approach, with downward retraction of the cerebellum 51 of an implantee 50 as shown by arrow 56 in FIG. 8. The elongate member 11 can be inserted from laterally to antero-medially. This direction of penetration is substantially perpendicular to the organization of the frequency layers 82 in the central nucleus of the inferior nucleus as shown by FIG. 7. The placement will preferably be performed at the same surgical setting, after removal of the acoustic neuroma. After implantation, the electrode lead 18 is preferably passed through an opening in the dura and can extend toward and preferably to the stimulator/receiver 21.

The second approach involves a medial sub-occipital (infratentorial-supracerebellar) approach. Using this approach, removal of an acoustic neuroma in an implantee with neurofibromatosis type 11 who has already lost his/her hearing and has multiple other tumours in the CNS is not absolutely necessary, unless the tumour is very large and has endangered other cranial nerves (such as the facial nerve) or is compressing the brainstem. In this approach after downward retraction of the cerebellum 51, direct exposure of the inferior colliculus is possible and the elongate member 11 can be placed under direct vision into the inferior colliculus.

The present invention provides an alternative system for providing hearing sensation to persons unable to derive any or sufficient benefit from traditional hearing aids or cochlear implants systems.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A brain stimulating electrode array for implantation into the inferior colliculus, the inferior colliculus having a central nucleus surrounded by an outer layer having a thickness and an exterior surface, the electrode array comprising:
   a substantially straight elongate member configured to be inserted into an inferior colliculus of an implantee, and having:
      a tip at a distal end of said elongate member configured to assist in passage of said member into the inferior colliculus and so as to cause minimal trauma to the inferior colliculus; and
      a plurality of electrodes wherein each of said electrodes comprises an operative edge that is substantially perpendicular to said elongate member, and wherein the plurality of electrodes are spaced apart from one another along said elongate member and configured to apply pre-selected tissue stimulation to one or more layers of the different frequency layers of the inferior colliculus; and
   a skirt radially extending from the elongate member, the skirt proximally spaced from a most proximal electrode of the plurality of electrodes by a distance approximately equal to the thickness of the outer layer.

2. The brain stimulating electrode array of claim 1, wherein said plurality of electrodes comprises between about 4 and 80 electrodes.

3. The brain stimulating electrode array of claim 2, wherein said plurality of electrodes comprises about 20 electrodes.

4. The brain stimulating electrode array of claim 1, wherein said plurality of electrodes are disposed in a longitudinal array on said elongate member.

5. The brain stimulating electrode array of claim 4, wherein said plurality of electrodes are equally spaced along said elongate member.

6. The brain stimulating electrode array of claim 1, wherein each of said plurality of electrodes comprises at least one single penetrating pin.

7. The brain stimulating electrode array of claim 1, wherein each of said plurality of electrodes is selected from a group comprising a ring, a half ring, a flat pad, and a multiple number of pins or pads around the circumference of said elongate member.

8. The brain stimulating electrode array of claim 7, wherein each of said plurality of electrodes are substantially identical in form.

9. The brain stimulating electrode array of claim 7, wherein at least one of said plurality of electrodes has a first form, and wherein at least one of said other electrodes has a second form.

10. The brain stimulating electrode array of claim 1, wherein each of said plurality of electrodes has a width of between about 50 microns and about 2000 microns.

11. The brain stimulating electrode array of claim 10, wherein each of said plurality of electrodes has a width of about 100 microns.

12. The brain stimulating electrode array of claim 1, wherein the spacing between each of said plurality of electrodes is between about 50 microns and about 2000 microns.

13. The brain stimulating electrode array of claim 12, wherein the spacing between each of said plurality of electrodes is about 100 microns.

14. The brain stimulating electrode array of claim 4, wherein said array has a length of between about 2 mm and about 6 mm.

15. The brain stimulating electrode array of claim 14, wherein said array has a length of about 4 mm.

16. The brain stimulating electrode array of claim 1, wherein the diameter of said elongate member begins to decrease proximate the distal end to said tip.

17. The brain stimulating electrode array of claim 16, wherein said tip is formed of a biocompatible material.

18. The brain stimulating electrode array of claim 1, wherein said elongate member has a body formed from a biocompatible material.

19. The brain stimulating electrode array of claim 18, wherein said elongate body has a diameter of about 0.2 mm to about 2 mm.

20. The brain stimulating electrode array of claim 19, wherein said elongate body has a diameter of about 0.5 mm.

21. The brain stimulating electrode array of claim 1, wherein said skirt is adapted to collapse on insertion of said elongate member through a delivery cannula but expand on exiting a distal end of the cannula.

22. The brain stimulating electrode array of claim 21, wherein said skirt is spaced a distance of between about 6 mm and about 6.5 mm from said distal tip and is adapted to stabilize said elongate member in a portion of the brain and ensure that said elongate member does not migrate further into said portion following correct placement.

23. The brain stimulating electrode array of claim 22, wherein said skirt has a plurality of fold lines and/or ribs formed therein so as to allow said skirt to collapse on insertion through the delivery cannula.

24. The brain stimulating electrode array of claim 23, wherein said skirt is adapted to collapse and/or expand in a spiral fashion.

25. The brain stimulating electrode array of claim 1, wherein said elongate member has a stiffening element extending at least partially therethrough.

26. The brain stimulating electrode array of claim 25, wherein said stiffening element is non-removably positioned in said elongate member.

27. The brain stimulating electrode array of claim 1, further comprising:
a lumen at least partially extending through said elongate member; and
a stiffening element removably positioned in at least a portion of said lumen to assist in implantation of said array.

28. The brain stimulating electrode array of claim 27, wherein said stiffening element comprises:
a removable wire stylet.

29. The brain stimulating electrode array of claim 27, wherein said stiffening element comprises:
a bioresorbable stylet configured to dissolve upon exposure to body fluid.

30. The brain stimulating electrode array of claim 27, wherein said stiffening element comprises:
a first portion positioned in said lumen having a first cross-section, and
a second portion connected to said first portion having a second cross-section that is larger than said first cross-section.

31. The brain stimulating electrode array of claim 1, wherein said elongate member comprises:
a lumen at least partially extending through said elongate member, wherein said lumen is configured for the delivery of bioactive agents to the inferior colliculus.

32. The brain stimulating electrode array of claim 1, wherein the skirt extends completely around a circumference of the electrode array.

* * * * *